United States Patent [19]

Hagen et al.

[11] Patent Number: 5,324,722

[45] Date of Patent: Jun. 28, 1994

[54] 2-, 3-, 5-, 8-, 10- AND/OR 11-SUBSTITUTED DIBENZOXAZEPINE COMPOUNDS, PHARMACEUTICAL COMPOSITIONS AND METHODS FOR TREATING PAIN

[75] Inventors: Timothy J. Hagen, Glenview; Michael Clare, Skokie; Michael F. Rafferty, Buffalo Grove; E. Ann Hallinan, Evanston, all of Ill.

[73] Assignee: G. D. Searle & Co., Chicago, Ill.

[21] Appl. No.: 58,834

[22] Filed: May 7, 1993

Related U.S. Application Data

[63] Continuation-in-part of Ser. No. 813,316, Dec. 20, 1991, abandoned.

[51] Int. Cl.$^5$ .................. A61K 31/55; C07D 267/20; C07D 281/16
[52] U.S. Cl. ..................... 514/211; 540/547
[58] Field of Search ................ 540/547; 514/211

[56] References Cited

U.S. PATENT DOCUMENTS

| 3,534,019 | 10/1970 | Coyne et al. | 540/547 |
|---|---|---|---|
| 3,624,104 | 11/1971 | Cusic et al. | 540/547 |
| 3,917,649 | 11/1975 | Mueller | 540/547 |
| 3,989,719 | 11/1976 | Mueller | 540/547 |
| 3,992,375 | 11/1976 | Mueller | 540/547 |
| 4,045,442 | 8/1977 | Mueller | 540/547 |
| 4,125,532 | 11/1978 | Mueller | 540/547 |
| 4,170,593 | 10/1979 | Mueller | 540/547 |
| 4,559,336 | 12/1985 | Mueller | 540/547 |
| 4,559,337 | 12/1985 | Mueller | 540/547 |
| 4,614,617 | 9/1986 | Mueller | 540/547 |
| 4,728,735 | 3/1988 | Belanger et al. | 540/488 |

FOREIGN PATENT DOCUMENTS

| 0012385 | 6/1980 | European Pat. Off. . |
| 0193822A2 | 9/1986 | European Pat. Off. ... C07D 267/20 |
| 0193822 | 9/1986 | European Pat. Off. . |
| 0218077 | 4/1987 | European Pat. Off. . |
| 0480641A1 | 4/1992 | European Pat. Off. ... C07D 223/20 |
| 1318032 | 2/1962 | France . |
| 1473716 | 4/1966 | France . |
| 6700603 | 7/1967 | Netherlands . |
| 1170322 | 11/1969 | United Kingdom . |
| 1331892 | 9/1973 | United Kingdom . |
| 1522003 | 8/1978 | United Kingdom . |

OTHER PUBLICATIONS

Tilek et al, Chemical Abstract vol. 62, No. 14707g (1964).

Geigy, J. R., Chem. Abstract vol. 66, No. 78117a (1966).

Drower, et al., "The Antiociceptive Effects of Prostaglandin Antagonists in the Rat," European Journal of Pharmacology, 133, 249–256 (1987).

J. H. Sanner, "Dibenzoxazepine Hydrazides as Prostaglandin Antagonists," Intra-Science Chem. Rept., vol. 6, No. 1, 1–9 (1972).

(List continued on next page.)

Primary Examiner—Mukund J. Shah
Assistant Examiner—Philip I. Datlow
Attorney, Agent, or Firm—Roberta L. Hastreiter; Roger A. Williams

[57] ABSTRACT

The present invention provides substituted dibenzoxazepine compounds of Formula I:

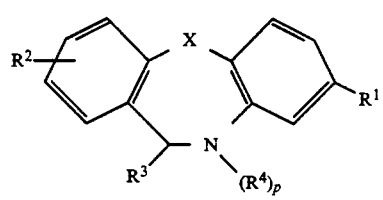

Formula I which are useful as analgesic agents for the treatment of pain, pharmaceutical compositions comprising a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

17 Claims, No Drawings

OTHER PUBLICATIONS

K. Nagarajan, et al., "Synthesis of 10,11-Dihydrodibenz[b,f][1,4]oxazepine Derivatives as Potential Anticonvulsants & Psychotropic Agents," *Indian Journal of Chemistry*, vol. 24B, 840–844 (1985).

D. E. MacIntyre, et al., "Antagonism of Human Platelet Responses to Stimulatory and Inhibitory Prostaglandins," *Prog. Lipid. Res.* 20 (1–4), 453–9 (1981).

R. Gimet, et al., "Quantitative Determination of Polymorphic Forms in a Formulation Matrix Using the Near Infra-Red Reflectance Analysis Technique," *J. Pharmaceutical & Biomedical Analysis*, vol. 5, No. 3, 205–211 (1987).

J. H. Sanner, et al., "Structure-Activity Relationships of some Dibenzoxazepine Derivatives as Prostaglandin Antagonists," *Advances in the Biosciences*, 9, 139–148 (1972).

A. Rakovska, et al., "Antagonistic Effect of SC-19220 on the Responses of Guinea-Pig Gastric Muscles to Prostaglandins E1, E2 and F2," *Arch. Int. Pharmacodyn.*, 268, 59–69 (1984).

W. E. Coyne, et al., "Anticonvulsant Semicarbazides," *J. Med. Chem.*, 11(6), 1158–1160 (1968).

K. Gyires, et al., "The Use of the Writhing Test in Mice for Screening Different Types of Analgesics," *Arch. Int. Pharmacodyn.*, 267, 131–140 (1984).

A. Bennett, et al., "Antagonism of Prostanoid-Induced Contractions of Rat Gastric Fundus Muscle by SC-19220, Sodium Meclofenamate, Indomethacin or Trimethoquinol," *Br. J. Pharmac.*, 71, 169–175 (1980).

C. A. Maggi, et al., "The Effect of SC-19220, a Prostaglandin Antagonist, on the Micturition Reflex in Rats," *European Journal of Pharmacology*, 152, 273–279 (1988).

George, et al., "Antagonism of Alcohol Hypnosis by Blockade of Prostaglandin Synthesis and Activity: Genotype and Time Course Effects," *Pharmacology Biochemistry & Behavior*, vol. 19, 131–136 (1983).

S. Nakajyo, et al., "Inhibitory Effect of Bassianolide, A Cyclodepsipeptide, on Drug-Induced Contractions of Isolates Smooth Muscle Preparations," *Japan. J. Pharmacol.*, 32, 55–64 (1982).

A. Gomes, et al., "Pharmacodynamics Venom of the Centipede *Scolopendra subspinipes dehaani*,"*Indian Journal of Experimental Biology*, vol. 20, 615–618 (1982).

2-, 3-, 5-, 8-, 10- AND/OR 11-SUBSTITUTED DIBENZOXAZEPINE COMPOUNDS, PHARMACEUTICAL COMPOSITIONS AND METHODS FOR TREATING PAIN

This is a Continuation-in-Part application of application Ser. No. 07/813,316, filed on Dec. 20, 1991, now abandoned.

BACKGROUND OF THE INVENTION

1. Field of the Invention

The present invention generally relates to compounds having pharmacological activity which are useful as pharmaceutical agents and, more particularly, as analgesic agents for the treatment of pain, to pharmaceutical compositions containing one or more of these compounds, and to methods of treatment employing these compounds. More particularly, the present invention concerns substituted dibenzoxazepine compounds, pharmaceutical compositions containing one or more of these compounds in combination with a pharmaceutically-acceptable carrier, and medical methods of treating pain employing these compounds.

Analgesic compounds are agents which alleviate pain without causing a loss of consciousness and, thus, which are useful for treating pain and, often, for reducing inflammation.

The major classes of analgesic compounds include narcotic analgesics, or opiates, compounds which alleviate pain and induce sleep, and analgesic-antipyretic compounds, compounds which alleviate pain and reduce fever,, such as salicylates.

Although the efficacy of opiates in relieving pain is well established, the associated addiction liability of opiates is a distinct disadvantage of these compounds.

While salicylate and salicylate-like agents (non-steroidal antiinflammatory agents or NSAIDS) are also efficacious in relieving pain, they often exhibit undesirable side effects, such as gastrointestinal irritation, as with aspirin, allergic response, as with aspirin, and/or liver toxicity with extended use, as with acetaminophen.

The compounds of the present invention are neither opiates nor salicylates, and represent another class of compounds which are useful as analgesic agents.

(2) Description of the Related Art

U.S. Pat. Nos. 4,559,336 and 4,614,617 (a continuation-in-part of U.S. Pat. No. 4,559,336) disclose 8-chlorodibenz[b,f][1,4]-oxazepine-10(11H)-carboxylic acid, 2-(sulfinyl- and sulfonyl-containing acyl)hydrazides, and intermediates thereof.

U.S. Pat. No. 3,534,019 discloses hydrazides of dibenzoxazepine-, dibenzothiazepine- and dibenzodiazepinecarboxylic acids.

U.S. Pat. No. 3,624,104 discloses aralkanoyl derivatives of dibenzoxazepine-N-carboxylic acid hydrazide compounds.

U.S. Pat. No. 3,989,719 discloses N,N'-diacyl hydrazines.

U.S. Pat. Nos. 3,917,649 and 3,992,375 (a divisional of U.S. Pat. No. 3,917,649) disclose dibenzoxazepine N-carboxylic acid hydrazine compounds.

U.S. Pat. Nos. 4,045,442, 4,125,532 (a divisional of U.S. Pat. No. 4,045,442) and U.S. Pat. No. 4,170,593 (a divisional of U.S. Pat. No. 4,125,532) disclose 1-(substituted amino)alkanoyl-2-(dibenzoxazepine-10-carbonyl)hydrazine compounds.

U.S. Pat. No. 4,559,337 discloses 8-chlorodibenz-[b,f][1,4]-oxazepine-10(11H)-carboxylic acid, 2-(alkoxy-containing acyl)hydrazide compounds.

GB 1 522 003 discloses 1-acyl-2-(8-chloro-10,11-dihydrodibenz[b,f][1,4oxazepine-10-carbonyl compounds.

GB 1 331 892 discloses derivatives of dibenzoxazepine N-carboxylic acid hydrazides.

European Patent Application Publication No. 0 012 385 discloses dibenz[b,f][1,4]oxazepine derivatives.

German Patent Application Publication No. 1,170,322 discloses 10-substituted dibenz[b,f][1,4oxazepin-11(10H)-ones.

European Patent Application Publication No. 0 193 822 discloses 8-chlorodibenz[b,f][1,4]-oxazepine-10(11H)-carboxylic acid, 2-(thio-, sulfinyl- and sulfonyl-containing acyl)hydrazide compounds.

European Patent Application Publication No. 0 218 077 discloses 8-chlorodibenz[b,f][1,4]oxazepine-10(11H)-carboxylic acid, 2-[(substituted phenylsulfinyl-)alkanoyl]hydrazide compounds and 8-chlorodibenz[b,f][1,4oxazepine-10(11H)-carboxylic acid, 2-[(substituted phenylsulfonyl)alkanoyl]hydrazide compounds, and intermediates used in the preparation of these compounds.

Netherlands Patent No. 67,00603 discloses substituted dibenz[b,f][1,4oxazepine-11(10H)-one compounds.

Drower et al., "The Antiociceptive Effects of Prostaglandin Antagonists in the Rat, " *European Journal of Pharmacology,* 133, 249–256 (1987), disclose the study of the antinociceptive properties of two competitive antagonists of prostaglandins of the E series, 8-chlorodibenz[b,f][1,4]-oxazepine-10(11H)-carboxylic acid, 2-acetylhydrazide and 8-chlorodibenz[b,f][1,4]-oxazepine-10(11H)-carboxylic acid, 2-(5-chloro-1-oxopentyl)-hydrazide.

J. H. Sanner, "Dibenzoxazepine Hydrazides as Prostaglandin Antagonists," *Intra-Science Chem. Rept.,* 6(1), 1–9 (1972), describes experiments performed with two dibenzoxazepine derivatives designated SC-18637 and SC-19220, and shown below, and found that SC-18637 and SC-19220 inhibit the stimulant actions of prostaglandins on isolated smooth muscle preparations.

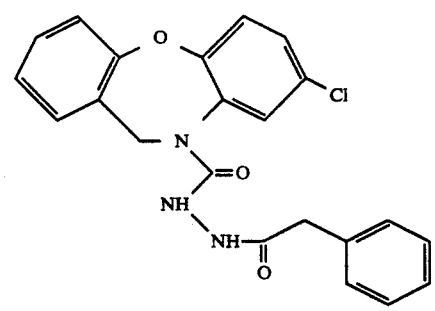

SC-18637

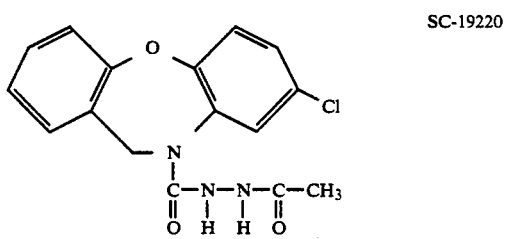

SC-19220

K. Nagarajan et al., "Synthesis of 10,11-Dihydrodibenz[b,f][1,4]oxazepine Derivatives as Potential Anticonvulsants & Psychotropic Agents," *Indian Journal of Chemistry*, 24B, 840-844 (985), disclose the synthesis of acyl, carbamoyl and thiocarbamoyl derivatives of 10,11-dihydrodibenz[b,f][1,4]oxazepine, most of which have either a nitro or an amino group at position-2, as analogues of carbamazepine, and the evaluation of these derivatives as anticonvulsants associated with neuroleptic activity.

Other art which relates to the present invention includes that which is discussed below.

D. E. MacIntyre et al., "Antagonism of Human Platelet Responses to Stimulatory and Inhibitory Prostaglandins," *Prog. Lipid. Res.* 20(1-4), 453-9 (1981), disclose on Page 454, Lines 11-12, Page 458, Lines 43-44, and in Table 1, two dibenzoxazepine compounds designated SC-19220 and SC-25191, and shown above and below, respectively, which were employed in an investigation of the effects of prostaglandin antagonists on platelet responses to stimulatory and inhibitory prostaglandins.

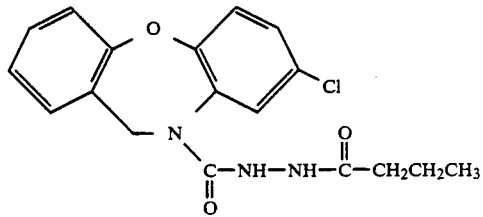

SC-25191

R. Gimet et al., "Quantitative Determination of Polymorphic Forms in a Formulation Matrix Using the Near Infra-Red Reflectance Analysis Technique," *J. Pharmaceutical & Biomedical Analysis*, 5 ( 3), 205-211 (1987), disclose an analytical method for the determination of the polymorphic transformation of an active ingredient in a solid dosage form matrix, and discuss a compound designated SC-25469, and shown below, at Page 206, Lines 16-23.

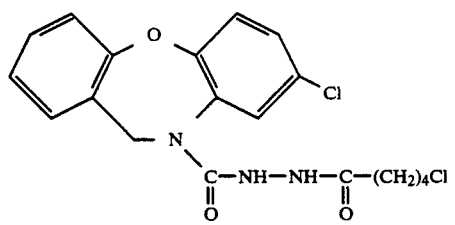

SC-25469

J. H. Sanner et al., "Structure-Activity Relationships of some Dibenzoxazepine Derivatives as Prostaglandin Antagonists," Advances in the Biosciences, 9, 139-148 (1972), disclose tests for prostaglandin antagonism on isolated guinea-pig ileum and rat stomach fundus strips with the n-butanoyl, i-butanoyl and n-hexanoyl analogs of SC-19220 and, on Page 140, Lines 11-18, show the chemical structures of the compounds used in the study.

A. Rakovska et al., "Antagonistic Effect of SC-19220 on the Responses of Guinea-Pig Gastric Muscles to Prostaglandins $E_1$, $E_2$ and $F_2$," *Arch. int. Pharmacodyn,* 268, 59-69 (1984), disclose a study of the contractile responses of guinea-pig gastric muscles to SC-19220, and the prostaglandin-blocking activity and specificity of SC-19220 on these muscles.

W. E. Coyne et al., "Anticonvulsant Semicarbazides," J. Med. Chem., 11(6), 1158-1160 (1968), disclose the investigation of the structure-activity relationship of the anticonvulsant activity of a series of semicarbazides which was synthesized from various tricyclic amines (see Table I, Page 1160).

K. Gyires et al., "The Use of the Writhing Test in Mice for Screening Different Types of Analgesics," *Arch. int. Pharmacodyn,* 267, 131-140 (1984), describe a comparison of the analgesic potency of some prostaglandin synthesis inhibitors, including SC-19220, and morphine using the writhing test. SC-19220 is discussed on Page 133, Lines 10 and 14-16, in Table II (Page 134), and on Page 135, Lines 16-25, and Page 137, Lines 34-38.

A. Bennett et al., "Antagonism of Prostanoid-Induced Contractions of Rat Gastric Fundus Muscle by SC-19220, Sodium Meclofenamate, Indomethacin or Trimethoquinol, " *Br. J Pharmac,* 71, 169-175 (1980), disclose the study of the effects of several compounds, including SC-19220, on contractions of the rat stomach longitudinal muscle to several prostanoids. SC-19220 is discussed on Page 175, Paragraph 1, Page 170, Paragraph 4, in Table 1 and FIG. 2, on Page 172, Paragraph 2, and on Page 174, Paragraphs 1 and 2.

C. A. Maggi et al., "The Effect of SC-19220, a Prostaglandin Antagonist, on the Micturition Reflex in Rats, " *European Journal of Pharmacology,* 152, 273-279 (1988), disclose a study in which SC-19220 is said to have increased the bladder capacity and reduced the voiding efficiency of micturition of urethane-anesthetized rats.

George et al , "Antagonism of Alcohol Hypnosis by Blockade of Prostaglandin Synthesis and Activity: Genotype and Time Course Effects," *Pharmacology Biochemistry & Behavior,* 19, 131-136 (1983), disclose a study of genetic and time-course factors of the effect of the antagonism of alcohol-induced behaviors of mice which have been pretreated with prostaglandin synthetase inhibitors and the effect of SC-19220 on ethanol sleep time.

S. Nakajyo et al., "Inhibitory Effect of Bassianolide, A Cyclodepsipeptide, on Drug-Induced Contractions of Isolated Smooth Muscle Preparations," *Japan. J. Pharmacol.,* 32, 55-64 ( 1982 ), disclose a study of the effect of bassianolide on the contractile responses induced by various types of neurotransmitters and autacoids. SC-19220 was employed in this study and is discussed on Page 57, Paragraph 1, in FIGS. 2 and 3, in Table 1, and on Page 60, Paragraph 1, Page 62, Paragraph 3, and Page 63, Paragraph 2.

A. Gomes et al., "Pharmacodynamics of Venom of the Centipede *Scolopendra subspinipes dehaani,*" *Indian Journal of Experimental Biology,* 20, 615-618 (1982), disclose an investigation of the pharmacodynamic actions of the venom of the tropical centipede *S. subspinipes.* SC-19220 was employed in this study and is discussed on Page 615 (abstract), Page 616, Line 30, Page 617, Lines 13-18, in FIGS. 4 and 5, and on Page 618, Lines 23-26.

Each of the documents described hereinabove discloses compounds which are structurally different from the compounds of the present invention. Thus, the compounds of the present invention are structurally distinct from that which has been described in the art.

Compounds of the present invention have been found to exhibit activity as prostaglandin $E_2$ antagonists.

SUMMARY OF INVENTION

The present invention provides compounds having a structure of Formula I:

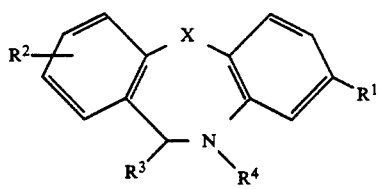

Formula I or a pharmaceutically-acceptable salt, ester of amide thereof, wherein:

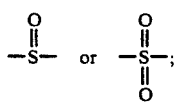

X is oxygen, sulfur
$R^1$ is hydrogen, halogen or haloalkyl;
$R^2$ is hydrogen, halogen, hydroxy or alkoxy;
$R^3$ is hydrogen, alkyl, carboxyl, carboxamide,

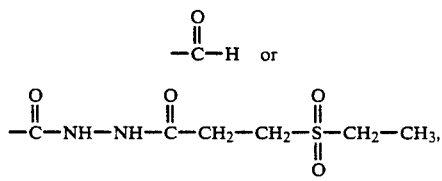

with the proviso that $R^3$ is not hydrogen or alkyl when $R^4$ is

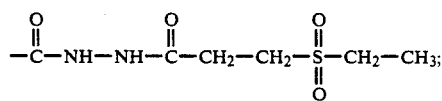

$R^4$ is hydrogen, alkoxycarbonyl or

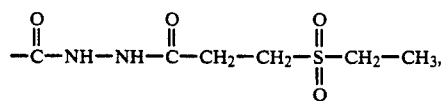

with the proviso that $R^4$ is hydrogen only when $R^3$ is alkoxycarbonyl.

The present invention also provides pharmaceutical compositions which are pharmaceutically acceptable and which comprise a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

DETAILED DESCRIPTION OF THE INVENTION (1) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The abbreviations "AcOH" and "HOAc" as used herein mean acetic acid.

The term "alkyl" as used herein means a saturated hydrocarbon radical having from one to ten carbon atoms, and within which includes from one to six carbon atoms, and further within which includes from one to three carbon atoms, which can be a straight or branched chain. Representative of such radicals are methyl, ethyl, propyl, isopropyl, butyl, sec-butyl, isobutyl, tert-butyl, pentyl and the like.

The term "alkoxy" as used herein means an alkyl radical, as defined above, having an oxygen atom attached thereto. Representative alkoxy groups include methoxy, ethoxy, propoxy, tert-butoxy and the like.

The term "alkoxycarbonyl" as used herein means an alkoxy group, as defined above, having a carbonyl group attached thereto, as defined below, for example

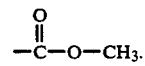

The abbreviation "AlMe₃" as used herein means trimethylaluminum.

The term "analgesia" as used herein means the reduction, or absence, of sensibility to pain, designating particularly the relief of pain without loss of consciousness.

The term "animal" as used herein includes humans and animals.

The abbreviation "Boc" as used herein means t-butyloxycarbonyl.

The abbreviation "Calc." as used herein means calculated.

The term "carbonyl" as used herein means a

group.

The term "carboxy" as used herein means a

group.

The term "carboxamide" as used herein means a

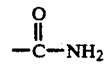

group.

The term "composition" as used herein means a product which results from the combining of more than one element or ingredient.

The abbreviation "DMAP" as used herein means 4-(dimethylamino)pyridine.

The abbreviation "DMF" as used herein means dimethylformamide.

The abbreviation E⁺ as used herein means electrophile.

The phrase "EC₅₀ concentration" as used herein means that concentration of a compound or drug which produces a 50% inhibition in a biological effect, such as contractions in isolated segments of guinea pig ileum.

The phrase "$ED_{50}$ dose" as used herein means that dose of a compound or drug which produced a biological effect, such as producing analgesia, in 50% of the animals to which the compound or drug was administered.

The abbreviation "Et" as used herein means ethyl (—$CH_2CH_3$).

The abbreviation "EtOAc" as used herein means ethyl acetate.

The abbreviation "EtOH" as used herein means ethanol ($CH_3CH_2OH$).

The abbreviation "$Et_3N$" as used herein means triethylamine.

The term "halo" or "halogen" as used herein means chlorine (Cl), bromine (Br), fluorine (F) and/or iodine (I).

The term "haloalkyl" as used herein means an alkyl radical, as defined above, which has one or more hydrogen atoms replaced by a halogen atom, as defined above, including, but not limited to, fluoromethyl, 2-chloroethyl, trifluoromethyl, 2,2-dichloroethyl and the like.

The term "heteroatom" as used herein means an atom of any element other than carbon or hydrogen.

The abbreviation "$^1$H NMR" as used herein means Proton Nuclear Magnetic Resonance.

The abbreviation "HPLC" as used herein means High Pressure Liquid Chromatography.

The term "hydroxy" as used herein means the group —OH.

The term "intragastrically" and/or the abbreviation "i.g." as used herein means that a compound or drug was administered into the stomach.

The abbreviation "i.p." as used herein means that a compound or drug was administered intraperitoneally.

The abbreviation "IR" as used herein means infrared (referring to an infrared spectrum).

The abbreviation "LAH" as used herein means lithium aluminum hydride.

The abbreviation "Me" as used herein means methyl (—$CH_3$).

The abbreviation "MeOH" as used herein means methanol ($CH_3OH$).

The abbreviation "mp" as used herein means melting point.

The abbreviation "MPLC" as used herein means Medium Pressure Liquid Chromatography.

The abbreviation "n-BuLi" as used herein means n-butyl lithium.

The abbreviation "NMR" as used herein means Nuclear Magnetic Resonance.

The abbreviation "n-Pr" as used herein means n-propyl.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, valerate, oleate, palmitate, stearate, laurate, benzoate, lactate, phosphate, tosylate, citrate, maleate, fumarate, succinate, tartrate, napsylate, clavulanate and the like salts, and alkali metal salts, such as sodium and potassium, and alkaline earth salts, such as calcium and magnesium.

The abbreviation "Pr" as used herein means propyl.

The abbreviation "p.o." as used herein means that a compound or drug was administered orally.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The phrase "N-protecting group" or "N-protected" as used herein means those groups intended to protect the N-terminus of an amino acid or peptide, to protect an amino group against undesirable reactions during synthetic procedures and includes, but is not limited to, sulfonyl, acetyl, pivaloyl, t-butyloxycarbonyl (Boc), carbonylbenzyloxy (Cbz), benzoyl and an L- or D-aminoacyl residue, which may itself be N-protected similarly.

The abbreviation "RaNi" as used herein means Raney nickel.

The abbreviation "s.c." as used herein means that a compound or drug was administered subcutaneously.

The abbreviation "t-Bu" as used herein means tert-butyl.

The abbreviation "TEA" as used herein means triethylamine.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The abbreviation "THF" as used herein means tetrahydrofuran.

The phrases "title compound," "title product" and "title material" as used herein mean that compound, product or material whose chemical name is given, and/or whose structure is shown, in the particular example, or subpart thereof, referred to. If no particular example, or subpart thereof, is referred to, it means that compound, product or material whose chemical name is given, and/or whose structure is shown, in the particular example, or subpart thereof, in which it appears.

(2) Description of Invention

In one aspect, the present invention provides compounds comprising a structure of Formula I, as described above, and pharmaceutically-acceptable salts, esters and amides thereof.

The compounds of the present invention comprise a class of substituted dibenzoxazepine compounds in which the 2, 3, 5, 8, 10 and/or 11-position is substituted. Compounds within the present invention have been shown to exhibit activity as prostaglandin $E_2$ antagonists.

Specific compounds within the scope of the invention include, but are not limited to, the compounds discussed in the examples presented below, as well as their pharmaceutically-acceptable salts, esters, and amides.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of this invention may exist in geometric or stereoisomeric forms. The present invention contemplates all such compounds, including cis- and trans- geometric isomers, R- and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Certain compounds of the present invention may contain a basic functional group, such as amino, alkylamino or dialkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, S. M. Berge et al., "Pharmaceutical Salts," *J Pharm Sci.*, 66, 1-19, (1977), which, as well as all other documents referred to herein, is incorporated herein by reference.)

In other cases, the compounds of the invention may contain one or more acidic functional groups, such as carboxyl and the like, and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., "Pharmaceutical Salts, supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. The pharmaceutical compositions of the invention may be specially formulated for oral administration in solid or liquid form, for parenteral injection, or for rectal or vaginal administration.

In yet a further aspect, the present invention provides a method for eliminating or ameliorating pain in an animal, or for producing some other therapeutic effect, as discussed in more detail hereinbelow, comprising administering a therapeutically-effective amount of a compound of Formula I, as described hereinabove, to the animal.

The most preferred embodiment of this invention is the compound described in Example 13 below.

(3) Utility

Compounds of the present invention exhibit activity as prostaglandin $E_2$ antagonists (prostaglandin antagonists of the $E_2$ series).

Compounds within the present invention, and the pharmaceutical compositions comprising one or more of these compounds, are useful as analgesic agents for the elimination or amelioration of pain in animals.

In addition to treating pain, these compounds and compositions would be useful in treating convulsions, ischemia and other central nervous system disorders, as well as osteoporosis, dysmenorrhea, asthma, enuresis, arrhythmia, urinary incontinence, gastric hypermotility, irritable bowel syndrome and diarrhea, by virtue of their activity as prostaglandin $E_2$ antagonists.

(4) Methods of Preparation

In general, the compounds of the present invention may be prepared by the methods illustrated in the following general reaction schemes, or by modifications thereof, using readily available starting materials, reagents and conventional synthesis procedures. Unless otherwise specified, the various substituents of the compounds are defined in the same manner as they are defined above in Formula I in the "Summary of Invention" section.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

General Reaction Scheme No. 1 shows that an N-protected dibenzoxazepine (where $R^4$ is Boc or some other alkoxycarbonyl group) substituted at the 2- or 3-position ($R^2$) with hydrogen, halogen, hydroxy or alkoxy, and substituted at the 8-position ($R^1$) with hydrogen, halogen or haloalkyl, is treated with n-butyl lithium. The reaction is quenched with the appropriate electrophile, resulting in an additional substitution at the 11-position, with $R^3$ being carboxy, alkoxycarbonyl or —CHO.

General Reaction Scheme No. 2 shows that aniline derivatives are reacted with $POCl_3$ and phosphoric acid to yield compounds which are substituted on the side chain ($R^3$) with methyl, ethyl or propyl. The resulting imine is reduced with sodium cyanoborohydride with the result that $R^4$ is hydrogen. The substituted dibenzoxazepine is reacted with phosgene followed by treatment with 3-(ethylsulfonyl)propanoic acid, hydrazide to yield the final product, wherein $R^3$ is alkyl, carboxy, carboxamide, alkylcarbonyl, —C—H or

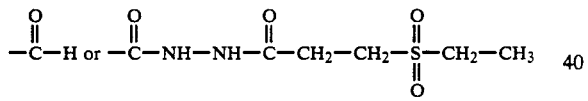

and $R^4$ is 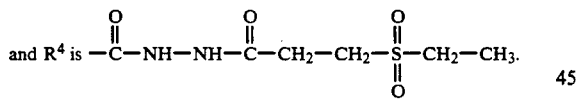

In General Reaction Scheme No. 3, 10-Boc-11-carbomethoxydibenzoxazepine is treated with 3-(ethylsulfonyl)propanoic acid, hydrazide and trimethylaluminum to yield the appropriate product. $R^1$ and $R^2$ are as defined above for General Reaction Scheme No. 1, $R^4$ is Boc and $R^3$ is

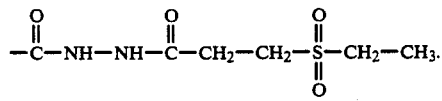

In each of the three general reaction schemes, X represents oxygen, sulfur,

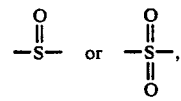

each of which is commercially available.

GENERAL REACTION SCHEME NO. I

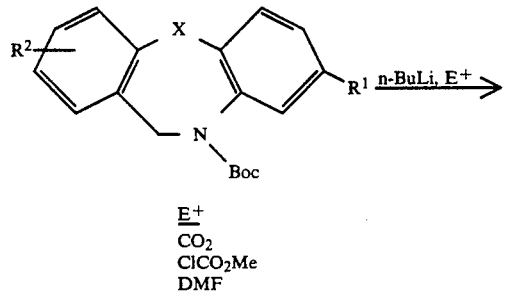

E+
$CO_2$
$ClCO_2Me$
DMF

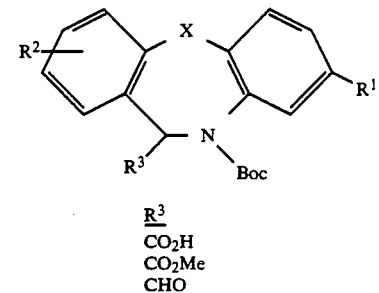

$R^3$
$CO_2H$
$CO_2Me$
CHO

GENERAL REACTION SCHEME NO. II

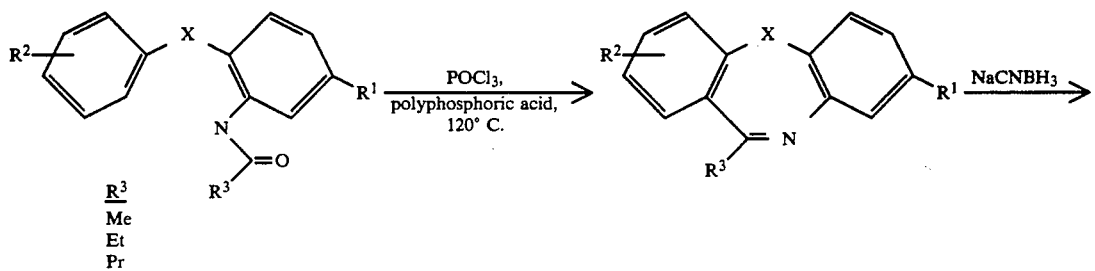

$R^3$
Me
Et
Pr

-continued
GENERAL REACTION SCHEME NO. II

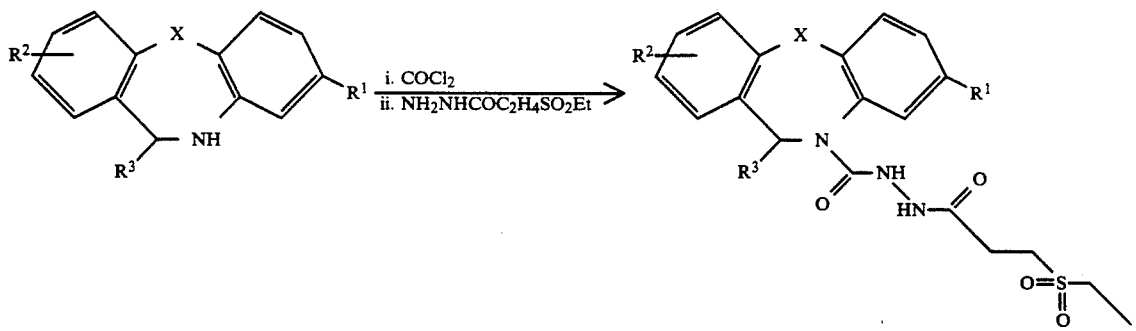

GENERAL REACTION SCHEME NO. III

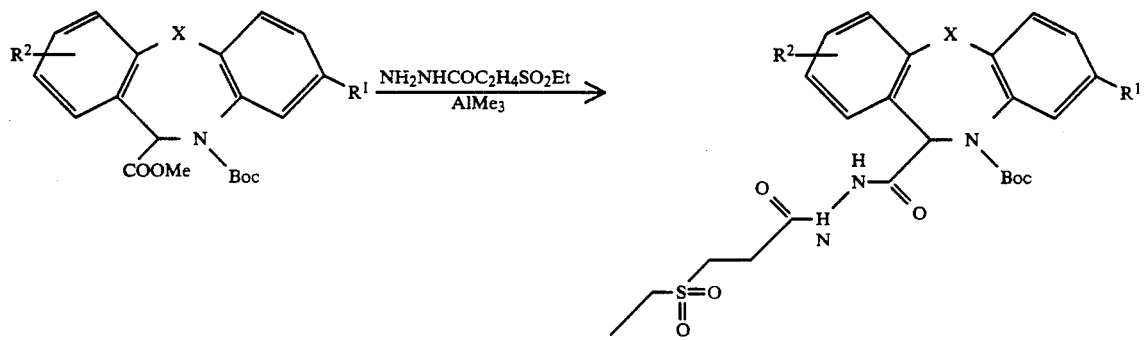

The conditions for carrying out the individual steps in each of the general reaction schemes presented above are conventional, well-known, and capable of wide variation.

Other methods known in the art can also be used to synthesize the compounds of the present invention.

(5) Dosage and Mode of Administration

The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally, the most preferred mode of administration is orally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, dosage levels in the range of from about 0.001 mg to about 10 g, more preferably from about 1 mg to about 1000 mg, of active compound per kilogram of body weight per day are administered to a mammalian patient. However, the total daily usage of the compounds of Formula I, or the pharmaceutical compositions comprising such compounds, will be determined by an attending physician or veterinarian within the scope of sound medical judgement.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, with one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium-carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient (compound of Formula I as described above), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Opthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

(6) Examples

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

In the examples, all parts are by weight unless otherwise indicated.

Most of the starting materials, and all of the equipment, employed in the examples are commercially available. Sources for these materials include Sigma Chemical Co. (St. Louis, Mo.), Aldrich Chemical Co. (Milwaukee, Wisc.), Lancaster Synthesis (Windham, NH), Fisher Scientific (Pittsburgh, Pa.), Boehringer Mannheim Biochemicals (Indianapolis, Ind.), Fluka Chemical Corp. (Ronkonkoma, N.Y.) and Chemical Dynamics Corp. (South Plainfield, N.J.). Most of the starting materials were obtained from Aldrich Chemical Co. (Milwaukee, Wisc.). The syntheses of those starting materials which are not commercially available are described in the examples presented below.

All patents and publications referred to in the examples, and throughout the specification, are hereby incorporated herein by reference, without admission that such is prior art.

EXAMPLE 1

8-chloro-10,11-dihydrobenz[b,f][1,4]oxazepine

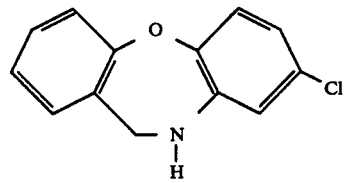

8-chloro-10,11-dihydrodibenz[b,f][1,4]oxazepine was prepared in the manner described in U.S. Pat. No. 3,534,019.

Briefly, 200 parts of 2,5-dichloro-nitrobenzene was heated to 160° C. and stirred, and 160 parts of the potassium salt of salicylaldehyde was added over a period of 30 minutes. After the addition was complete, an exothermic reaction took place, and the temperature rose to about 195° C. Heating was discontinued until the reaction subsided, and the mixture was heated for 1 hour at 150° C. The mixture was cooled, ice and water were added, and it was extracted with ether. The ether layer was filtered to remove insoluble material and the resultant solution was dried over sodium sulfate. The ether solvent was evaporated and the residual oil was recrystallized from a mixture of hexane and benzene to give 2-(2-nitro-4-chloro-phenoxy)benzaldehyde melting at about 100°–101° C.

A solution of 55 parts of the ether obtained in the preceding paragraph in 800 parts of ethanol was hydrogenated over Raney nickel catalyst at room temperature and atmospheric pressure. When hydrogen uptake ceased, the catalyst was removed by filtration, and the ethanol solvent was evaporated. The residue was then dissolved in 500 parts by volume of hexane, filtered, and cooled. There was then obtained yellowish-white crystals which were separated by filtration to give 8-chloro-10,11-dihydrodibenz[b,f][1,4]oxazepine melting at about 94°–95° C.

EXAMPLE 2

1,1-dimethylethyl 8-chlorodibenz[b,f][1,4]oxazepine-10(11H)-carboxylate

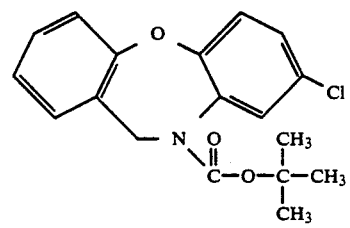

A solution of the title compound of Example 1 (15.0 g, 65 mmol), ditertbutyldicarbonate (17 g, 78 mmol) and DMAP (1 g, 8 mmol) in THF (500 mL) was refluxed under an $N_2$ atmosphere for 24 hours. The solvent was removed under reduced pressure to yield a yellow oil that was flash chromatographed on silica gel (10% EtOAc/hexane) to yield the title compound as a white solid (20.5 g, 95.4%).

Analysis calculated for $C_{18}H_{18}NO_3Cl$ (M.W. 331.8): C, 65.16; H, 5.47; N, 4.22. Found: C, 64.78; H, 5.51; N, 4.13.

EXAMPLE 3

8-chlorodibenz[b,f][1,4]oxazepine-10,11(11H)dicarboxylic acid. 10-(1,1-dimethylethyl) ester

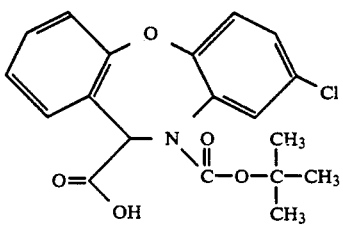

A stirring solution of the title compound of Example 2 (225 mg, 0.68 mmol) in 5 mL of THF was cooled to −78° C., followed by the addition of n-BuLi (1.5 M, 0.54 mL, 0.82 mmol). Upon the addition of the n-BuLi, a red solution resulted. The mixture was stirred at −78° C. for 30 minutes, and then $CO_2$ gas was passed through the reaction mixture while the reaction mixture was slowly warmed to 0° C. and diluted with 2 mL of HCl (1 M). The mixture was extracted with ether (50 mL) and washed with brine (25 mL×3), and the ether extract was dried ($Na_2SO_4$). The extract was concentrated to give the crude product (269 mg), which was purified by flash column chromatography with 10% EtOH/CHCl$_3$ (170 mg) to yield the title compound.

Analysis calculated for $C_{19}H_{18}NO_5Cl \times 1$ $H_2O$ (M.W. 363.8): C, 57.94; H, 5.12; N, 3.56; Cl, 9.00. Found: C, 58.21; H, 4.95; N, 3.27; Cl, 8.86.

EXAMPLE 4

8-chlorodibenz[b,f][1,4]oxazepine-10,11(11H)dicarboxylic acid, 10-(1,1-dimethylethyl)-11-methyl ester

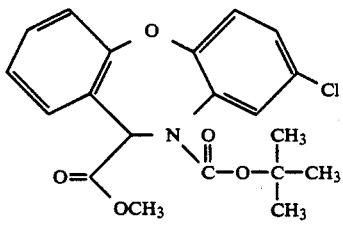

To a stirring solution of the title compound of Example 2 (10.0 g, 30 mmol) under $N_2$ at −78° C. was added n-BuLi (33 mmol). The resulting red solution was stirred at −78° for 15 minutes, followed by the addition of methyl chloroformate (33 mmol). The resulting light orange colored solution was allowed to warm to room temperature over a period of 1 hour. The reaction solution was poured onto CHCl$_3$ (1 L) and extracted with brine (4×250 mL). The CHCl$_3$ was dried (MgSO$_4$) and stripped to yield a yellow oil. The oil was chromatographed (MPLC, 85% hexane:15% EtOAc), and reinjected to yield 1.0 g of the title compound.

The title compound was employed in Example 5 without further purification.

EXAMPLE 5 methyl 8-chloro-10,11-dihydrodibenz[b,f][1,4]oxazepine-11-carboxylate

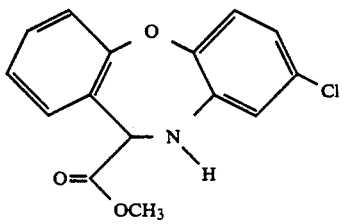

To a stirring solution of the title compound of Example 4 (210 mg, 0.54 mmol) in methylene chloride (25 mL) was added HCl/dioxane (1 mL, 6.95 mmol). The solution was stirred for 1 hour, followed by the removal of the solvent. The residue was solidified from ether and washed with hexane. The material was dried for 6 hours at 60° C. under vacuum to yield the title compound (150 mg).

Analysis calculated for $C_{15}H_{12}NO_3Cl$ (M.W. 289.7): C, 62.19; H, 4.18; N, 4.84. Found: C, 61.92; H, 4.38; N, 4.71.

EXAMPLE 6

3-(ethylsulfonyl)propanoic acid, hydrazide

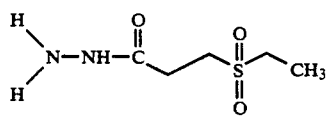

Methyl 3-(ethylsulfonyl)propanoate was prepared in the manner described in "Sulfinic Acids. I.," *Chemical Abstracts*, 51 (F03), 1064 (1956). The addition of sulfinic acids to an α,β-unsaturated compound (esters, ketones, amides, nitriles) results in sulfones. The reaction is conducted in an aqueous solution in the presence of NaH$_2$PO$_4$ (0.11 mole per 0.1 mole of Na salt of the sulfinic acid and 0.12 mole of the α,β-unsaturated compound in 200 mL of water).

To a stirring solution of methyl 3-(ethylsulfonyl)propanoate (10 mmol) in ethanol (30 mL) was added hydrazine monohydrate (15 mmol), and the resulting solution was stirred for 16 hours. The resulting precipitate was collected to yield the title compound as a white solid (52%). This material was employed in example 7 without further purification.

EXAMPLE 7

8-chlorodibenz[b,f][1,4]oxazepine-10,11(11H)-dicarboxylic acid, 10-(1,1-dimethylethyl) ester, 11-[2-[3-(ethylsulfonyl)-1-oxopropyl]hydrazide]

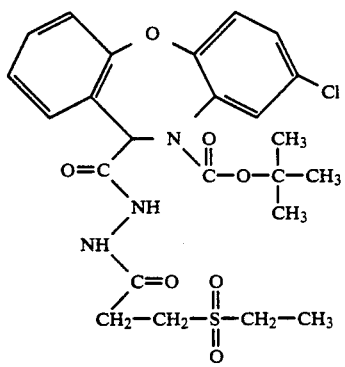

To a solution of the title compound of Example 4 (540 mg, 1.4 mmol) and the title compound of Example 6 (260 mg, 1.4 mmol) in toluene was added AlMe3 (4.0 mmol) in toluene (100 mL). The resulting yellow solution was refluxed under an N2 atmosphere for 20 hours. The reaction solution was cooled and EtOAc (500 mL) was added. The resulting organic solution was extracted with NaHCO3 (3×200 mL), dried (MgSO4) and removed under reduced pressure to yield 1.15 g of a gummy yellow solid. This material was chromatographed (MPLC, silicagel 4:1, EtOAc:hexane), followed by recrystallization from hexane/ether to yield the title compound as a white solid (70 mg) (melting point: 110°-112° C.

Analysis calculated for C24H28N3SO7Cl×0.25 H2O (M.W. 538): C, 53.92; H, 5.30; N, 7.75. Found: C, 52.92; H, 5.25; N, 7.69.

EXAMPLE 8

4-chloro-2-nitro-1-phenoxybenzene

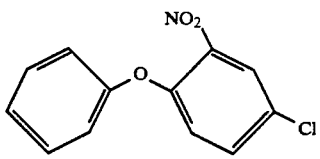

To a stirred solution of phenol (36.6 g, 0.39 mol) in DMF (250 mL) was added sodium hydride (10 g, 0.42 mol) in portions. To the resulting solution was added a solution of 2,5-dichloronitrobenzene (68 g, 0.35 mol) in DMF (500 mL), and the mixture was stirred for 16 hours. The solvent was removed under reduced pressure, and the residue was takene up in EtOAc (400 mL) and extracted with brine (saturated, 400 mL). The product was distilled to yield a yellow liquid (84.2 g, 95%), which had a boiling point of 245°-265° C./1.5 mmHg. This material was employed in Example 9 without further purification.

EXAMPLE 9

5-chloro-2-phenoxybenzenamine

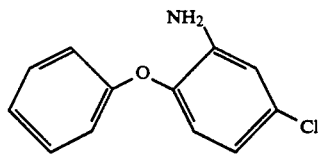

The title compound of Example 8 (76 g, 0.3 mol) was hydogenated with RaNi in THF (2.4 L). The product was distilled to yield a yellow liquid (69.5 g, 100%), which had a boiling point of 145°-150° C./1.5 mmHg. This material was employed in Example 10 without further purication.

EXAMPLE 10

N-(5-chloro-2-phenoxyphenyl)acetamide

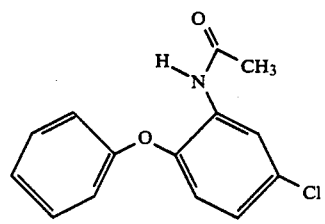

To a stirring compound of the title compound of Example 9 (5.0 g, 23 mmol) in pyridine (50 mL) was added acetic anhydride (2.75 g, 27 mmol), and the resulting solution was stirred for 3 hours. The solvent was removed under reduced pressure and the residue was dissolved in CHCl3 (300 mL) and extracted with HCl (1M, 3×150 mL), NaHCO3 (saturated, 3×150 mL), dried (MqSO4) and evaporated to yield an oil. The material was chromatographed (MPLC, 1:1 EtOAc:hexane) to yield 4.52 g of a yellow oil. This material was employed in Example 11 without further purication.

EXAMPLE 11

8-chloro-11-methyldibenz[b,f][1,4]oxazepine

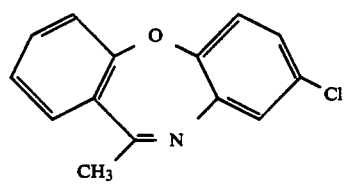

A mixture of the title compound of Example 10 (4.0 g, 15.2 mmol), polyphosphoric acid (32 mL) and POCl3 (5.6 mL) was heated to 120° C. with stirring for 2 hours. After cooling, the reaction mixture was poured onto 100 g of ice and extracted with CHCl3. The organic extracts were combined and washed with NaHCO3 and brine, dried over Na2SO4 and evaporated to yield the title compound.

EXAMPLE 12

8-chloro-10,11-dihydro-11-methyldibenz[b,f][1,4]oxazepine

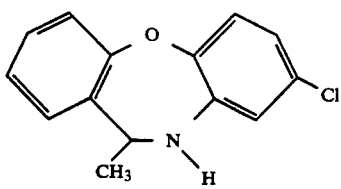

To a stirring solution of the title compound of Example 11 (3.20 g, 12 mL) in THF (100 mL) was added NaCNBH$_3$ (1.0 g, 16 mmol) in one portion. The resulting solution was stirred at room temperature for 3½ hours. The THF was removed under reduced pressure, and to the residue was added CHCl$_3$ (200 mL) and HCl (0.5N, 100 mL). The mixture was stirred for 15 minutes. The pH was adjusted to 8 with solid NaHCO$_3$. The layers were separated, and the aqueous layer was washed with CHCl$_3$ (100 mL). The organic layers were combined, dried, chromatographed (silicagel, CHCl$_3$) and evaporated to yield the title compound as an oil (2.67 g).

EXAMPLE 13

8-chloro-11-methyldibenz[b,f][1,4]oxazepine-10(11H)-carboxylic acid, 2-[3-(ethylsulfonyl)-1-oxopropyl]hydrazide

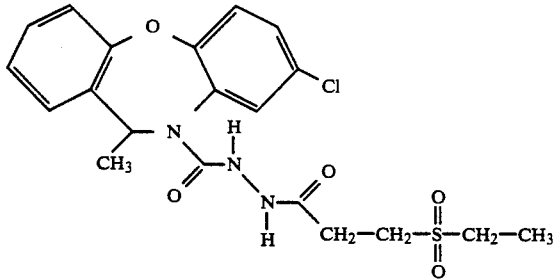

To a stirring solution of the title compound of Example 7 (2.0 g, 8.1 mmol) in THF (70 mL) and Et$_3$N (7 mL) was added phosgene (10.1 mL) in toluene. The reaction was stirred at 0° C., and then warmed for 1 hour. The reaction was filtered to remove triethylamine hydrochloride, washed with THF (100 mL), and the solvent was removed to yield a yellowish solid. To the solid was added toluene (50 mL), TEA (2 mL) and the title compound of Example 6 (1.6, 8.8 mmol), and the resulting solution was refluxed for 2½ hours. The reaction solution was cooled, filtered, washed with CHCl$_3$ and evaporated to yield a gummy solid. The material solidified to yield 4.77 g of a yellow solid that was chromatographed (HPLC, silicagel, CHCl$_2$, THF 1:1) to yield 1.05 g of a gummy foam. The material was crystallized from EtOAc to yield 320 mg of the title compound as a white solid.

Analysis calculated for C$_{18}$H$_{22}$N$_3$O$_5$SCl×0.25 H$_2$O (M.W. 427.89): C, 52.62; H, 5.02; N, 9.21. Found: C, 52.41; H, 4.90; N, 9.07.

The enatiomers of the title compound were separated on a chiralcel OC column (Daicel Chemical Industries LTD, Fort Lee, NJ) using 80/20 EtOH/hexane as eluent and 100 mg of sample.

Example 13A eluted first to yield 40 mg which was 97.779% pure by HPLC, $a_D = -145°$ at 589 nM.

Example 13B eluted second to yield 62 mg which was 80.5% pure by HPLC, $a_D = +66°$ at 589 nM.

8-chloro-11R-methyldibenz[b,f][1,4]-oxazepine-10(11H)-carboxylic acid, 2-[3-(ethylsulfonyl)-1-oxopropyl]hydrazide
Example 13A

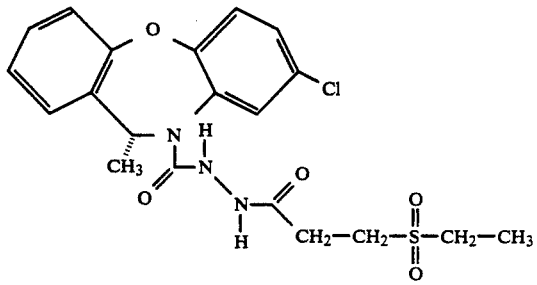

8-chloro-11S-methyldibenz[b,f][1,4]-oxazepine-10(11H)-carboxylic acid, 2-[3-(ethylsulfonyl)-1-oxopropyl]hydrazide
Example 13B

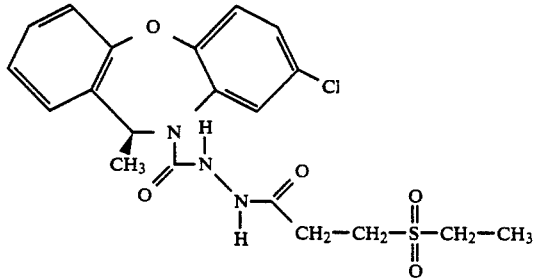

EXAMPLE 14

N-(5-chloro-2-phenoxyphenyl)propanamide

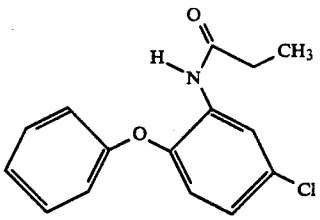

To a stirring solution of the title compound of Example 9 (5.0 g, 23 mmol) in pyridine (50 mL) was added propionic anhydride (3.51g, 27 mmol), and the resulting solution was stirred for 3 hours. The solvent was removed under reduced pressure and the residue was dissolved in CHCl$_3$ (300 mL) and extracted with HCl (1M, 3×150 mL), NaHCO$_3$ (saturated, 3×150 mL), dried (MgSO$_4$) and evaporated to yield an oil which crystallized on standing to yield 5.3 g of a white solid. This material was employed in Example 15 without further purication.

EXAMPLE 15

8-chloro-11-ethyldibenz[b,f][1,4]oxazepine

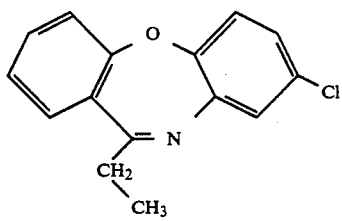

A mixture of the title compound of Example 14 (5.3 g), polyphosphoric acid (35 mL) and POCl$_3$ (7.0 mL) was heated at 120° C. for 2 hours. The resulting hot tar was poured onto CHCl$_3$/H$_2$O. The CHCl$_3$ was separated, washed with NaHCO$_3$, dried (MgSO$_4$) and evaporated to yield a reddish gum (5.3 g). The material was purified by chromatography to yield 1.79 g of the title compound.

Analysis calculated for C$_{15}$H$_{12}$NOCl×0.1 H$_2$O (M.W. 257.72): C, 69.42; H, 4.74; N, 5.48. Found: C, 69.28; H, 4.85; N, 5.26.

EXAMPLE 16

8-chloro-11-ethyl-10,11-dihydrodibenz[b,f][1,4]oxazepine

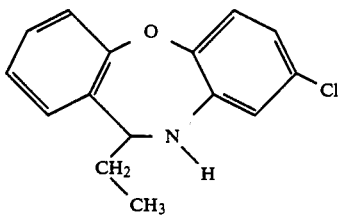

To a stirring solution of the title compound of Example 15 in THF was added NaCNBH$_3$. The reaction was stirred for 24 hours at room temperature. The solvent was removed under reduced pressure, and the residue was taken up in CHCl$_3$ with HCl (1M, 25 mL). The resulting mixtures were stirred for 1 hour at room temperature. The CHCl$_3$ was separated, extracted with NaHCO$_3$ (saturated) and brine. The solvent was removed to yield a yellow oil (2.06 g). The material was purified by column chromatography on silicagel 15/85 EtOAc/hexane to yield 1.06 g of the title compound. This material was employed in Example 17 without further purification.

EXAMPLE 17

8-chloro-11-ethyldibenz[b,f][1,4]oxazepine-10(11H)-carboxylic acid, 2-[3-(ethylsulfonyl)-1-oxopropyl]hydrazide

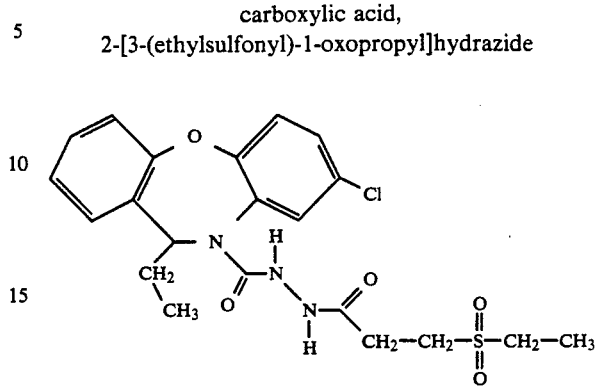

To a stirring solution of the title compound of Example 16 (1.1 g) in THF (50 mL) and Et3N (4 mL) was added phosgene in toluene (7.2 mmol, 3.8 mL). The reaction was stirred at 0° C. and then warmed for 1 hour at room temperature. The reaction mixture was filtered, washed with THF (100 mL), and the solvent was removed under reduced pressure to yield a yellowish solid. To the residue was added toluene (75 mL), TEA (4 mL) and the title compound of Example 6 (2.27 g), and the resulting reaction mixture was refluxed overnight. To the reaction solution was added EtOAc (300 mL), followed by washing with HCl (1N, 3×300 mL), NaHCO$_3$ (3×200 mL) and brine (1×200 mL). The organic materials were dried (Na$_2$SO$_4$) and evaporated to yield 1.3 g of a yellow gummy solid. The material was chromatographed (MPLC, 25% THF; 75% CHCl$_3$) to yield 450 mg the title compound as a white solid. Analysis calculated for C$_{21}$H$_{24}$N$_3$O$_5$Cl (M.W. 465.96): C, 54.13; H, 5.19; N, 9.02; Cl, 7.61; S, 6.88. Found: C, 54.52; H, 5.41; N, 8.90; Cl, 7.54; S, 6.77.

EXAMPLE 18

N-(5-chloro-2-phenoxyphenyl)butanamide

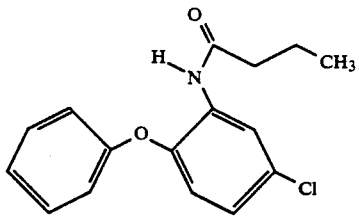

To a stirring solution of the title compound of Example 9 (5.0 g, 23 mmol) in pyridine (50 mL) was added butyric anhydride (4.3 g, 27 mmol), and the resulting solution was stirred for 3 hours. The solvent was removed under reduced pressure, and the residue was dissolved in CHCl$_3$ (300 mL) and extracted with HCl (1M, 3×150 mL), NaHCO$_3$ (saturated, 3×150 mL), dried (MgSO$_4$) and evaporated to yield an oil which crystallized on standing to yield 6.1 g of a white solid. This material was employed in Example 19 without further purication.

EXAMPLE 19

8-chloro-11-propyldibenz[b,f][1,4]oxazepine

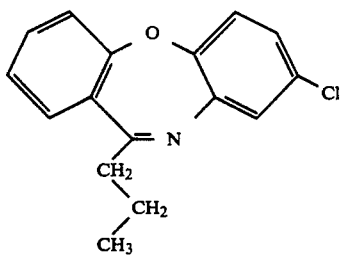

A mixture of the title compound of Example 18 (6.1 g), polyphosphoric acid (40 mL) and POCl$_3$ (9.0 mL) was heated at 120° C. for 2 hours. The resulting tar was portioned between water and CHCl$_3$. The CHCl$_3$ was separated and extracted with NaHCO$_3$. The solvent was removed to yield an orange gum (5.7 g). The product was purified by chromatography to yield 2.61 g of the title compound as an oil.

Analysis calculated for C$_{16}$H$_{14}$NOCl×0.25 H$_2$O (M.W. 271.74): C, 69.56; H, 5.29; N, 5.07. Found: C, 69.97; H, 5.31; N, 5.01.

EXAMPLE 20

8-chloro-10,11-dihydro-11-propyldibenz[b,f][1,4]oxazepine

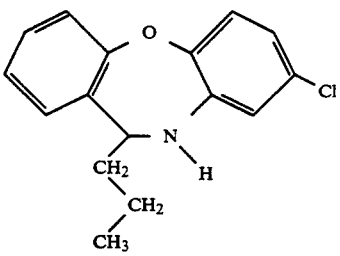

To a stirring solution of the title compound of Example 19 (2.6 g) in THF (100 mL) was added NaCNBH$_3$ (1.0 g). The reaction was stirred for 24 hours. The solvent was removed under reduced pressure, and the residue was taken up in CHCl$_3$ with HCl (1M, 25 mL). The resulting mixture was stirred for 1 hour at room temperature. The CHCl$_3$ was separated, extracted with NaHCO$_3$ (saturated) and brine. The solvent was then removed to yield a yellow oil (2.5 g). This material was purified by column chromatography to yield 1.7 g of the title compound. This material was employed in Example 21 without further purification.

EXAMPLE 21

8-chloro-11-propyldibenz[b,f][1,4]oxazepine-10(11H)-carboxylic acid.
2-[3-(ethylsulfonyl)-1-oxopropyl]hydrazide

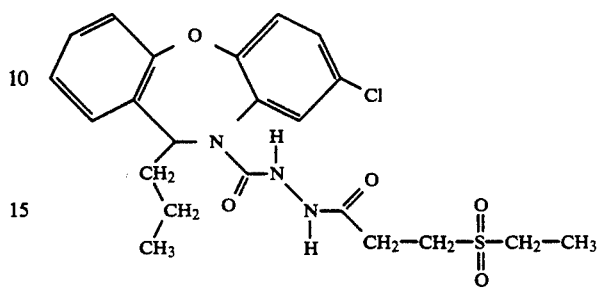

To a stirring solution of the title compound of Example 20 (1.76 g) in THF (50 mL) and Et$_3$N (6 mL) was added phosgene in toluene (11.3 mmol, 6 mL). The reaction was stirred at 0° C. for 1 hour, and then warmed and stirred at room temperature for 1 hour. The reaction mixture was filtered, washed with THF (100 mL), and the solvent was removed under reduced pressure to yield a yellow solid. To the residue was added toluene (75 mL), Et$_3$N (4 mL) and the title compound of Example 6 (2.27 g). The resulting mixture was stirred overnight at reflux. To the reaction solution was added EtOAc (300 mL) followed by washing with HCl (1N, 3×300 mL), NaHCO$_3$ (3×200 mL) and brine (1×200 mL). The organic materials were dried (Na$_2$SO$_4$) and evaporated to yield a white solid. The material was chromatographed (MPLC, 25% THF/75% CHCl$_3$) to yield 650 mg of the title compound as a white solid.

Analysis calculated for C$_{22}$H$_{26}$N$_3$O$_5$Cl (M.W. 479.99): C, 55.05; H, 5.46; N, 8.75; S, 6.68; Cl, 7.39. Found: C, 54.71; H, 5.68; N, 8.45; S, 6.13; Cl, 8.50.

The foregoing examples are provided to enable one of ordinary skill in the art to practice the present invention. These examples are merely illustrative, however, and should not be read as limiting the scope of the invention as it is claimed in the appended claims.

(7) The Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse orrat. [Gyires et al., *Arch. int. Pharmacodyn*, 267, 131–140 (1984); C. Vander Wende et al., *Fed. Proc.*, 15, 494 (1956); Koster et al., *Fed. Proc.*, 18, 412 (1959); and Witken et al., *J. Pharmacol. exp. Ther.*, 133, 400–408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table 1 below.

Charles River male albino mice, weighing 20 to 30 grams were used in this assay.

Thirty minutes after subcutaneous or intragastric administration to ten mice of 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the number of writhes occurring during the following ten-minute period was counted.

A test compound was considered to have produced analgesia in a mouse if, in accordance with the conditions set forth above, and under the test criteria employed for this assay, after the administration of 30 mg per kilogram of body weight of a compound of the present invention to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," *Advances in Biochemical Psychopharmacology*, 8, 191 (1974).

The results for the particular compounds of the present invention analyzed in this assay, and discussed in the examples identified below which correspond thereto, are presented in Table 1 hereinbelow under the heading "WRITHING ASSAY." The numbers in fractions indicate the number of mice out of ten in which a test compound produced analgesia. 8-chlorodibenz[b,f][1,4]-oxazepine-10,11(11H)-dicarboxylic acid, 10-(1,1-dimethylethyl) ester, 11-[2-[3-(ethylsulfonyl)-1-oxopropyl]-hydrazide](Example 7) and 8-chloro-11-methyl-dibenz[b,f][1,4]oxazepine-10(11H)-carboxylic acid, 2-[3-(ethylsulfonyl)-1-oxopropyl]hydrazide (Example 13) were determined to be the most potent compounds of the invention tested in this assay and, thus, are preferred compound of the present invention. (b) Prostaglandin (PGE) Antagonism Assay In order to determine the effectiveness of several of the compounds of the present invention ("test compounds") as prostaglandin $E_2$ antagonists, a prostaglandin antagonism assay was conducted, as described below, to determine the ability of these compounds to inhibit prostaglandin $E_2$-induced contractions of segments of guinea pig ileum. If a test compound inhibits prostaglandin $E_2$-induced contractions, it suggests that the compound functionally antagonizes prostaglandin $E_2$.

Male albino guinea pigs weighing 200 to 500 grams were sacrificed by cervical dislocation. The ilea were then quickly removed from the guinea pigs and placed in a modified Tyrode solution, a solution which is known to those skilled in the art, containing one-half of the usual amount of magnesium ions.

Segments of ileum about 2 cm long were then cut and mounted in a 10 mL tissue bath containing the modified Tyrode solution. The solution was maintained at 37° C. and aerated with a gaseous mixture of 95% oxygen and 5% carbon dioxide. Data for a control prostaglandin $E_2$ dose response curve plotting concentration of prostaglandin $E_2$ versus the intensity of contractions, detected isotonically, was then obtained by experimentally adjusting the dose of the prostaglandin $E_2$ being injected into the tissue bath, in a manner known by those of skill in the art.

Solutions or suspensions containing an initial concentration (3 micromolar) of a test compound in modified Tyrode solution ("test solutions/suspensions") were then separately substituted for the control bath solution. Each test solution/suspension was then kept in constant contact with the ileum tissue, except for brief periods to drain the bath in preparation for rinsing with fresh test solution/suspension. A second prostaglandin $E_2$ dose response curve was then generated for prostaglandin $E_2$ in the presence of a test compound.

A dose ratio of $EC_{50}$ doses was then calculated from the results of each test in a manner known by those of skill in the art. A test compound was determined to be "active" if the initial concentration used yielded at least a two-fold shift (dose ratio greater than or equal to 2) in the dose response curve for 10 prostaglandin $E_2$. An estimated $pA_2$ value (a statistical constant which is a common measure of expressing the potency of a particular drug as an antagonist) was reported for "active" compounds under the assumption that the slope of the Schild plot does not deviate significantly from $-1.0$. If the initial concentration of test compound yielded at least a five-fold shift (dose ratio greater than or equal to 5) in the dose response curve for prostaglandin $E_2$, then varying concentrations of the test compound were assayed, and a $pA_2$ value for that compound was calculated by Schild plot calculations, as described by H. O. Schild, "pA, A New Scale for the Measurement of Drug Antagonism," Br. J. pharmacol, 2, 189 (1947). The higher the value calculated for the $pA_2$, the more potent a particular compound is as a prostaglandin $E_2$ antagonist.

The results of this prostaglandin antagonism assay are also presented in Table 1 below. The compounds of the present invention which were tested in this assay, and for which results are presented in Table 1, correspond to the particular examples specified in Table 1.

TABLE 1

| Example Number | Data Generated from the Assays | | PGE ANTAGONISM IN GUINEA PIG ILEUM |
|---|---|---|---|
| | WRITHING ASSAY Number Out of Ten | | |
| | S.C. | I.G. | |
| Example 13 | 5/10 | 5/10 | 6.03 |
| Example 7 | 3/10 | 5/10 | * |
| Example 21 | 1/10 | 3/10 | 5.94 |
| Example 17 | 2/10 | 1/10 | 5.89 |

* — Indicates that, in accordance with the particular conditions set forth above in the Prostaglandin Antagonism Assay, and under the test criteria employed for that assay, after the administration of an initial screening dosage of 3 micromolar of the compound, a two-fold shift in the dose response curve for prostaglandin $E_2$ was not yielded.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A compound having a structure:

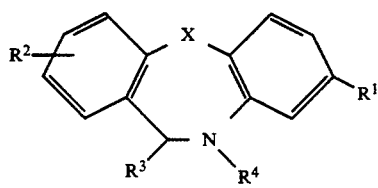

or a pharmaceutically-acceptable salt, ester or amide thereof, wherein:

X is oxygen, sulfur,

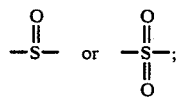

$R^1$ is hydrogen, halogen or haloalkyl;
$R^2$ is hydrogen, halogen, hydroxy or alkoxy;
$R^3$ is hydrogen, alkyl, carboxyl, carboxamide,

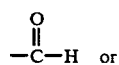 or

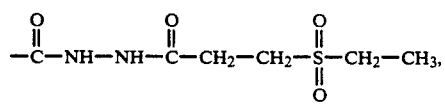

wherein the proviso that $R^3$ is not hydrogen or alkyl when $R^4$ is

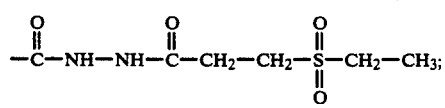

$R^4$ is hydrogen, alkoxycarbonyl or

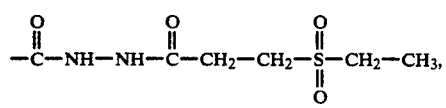

with the proviso that $R^4$ is hydrogen only when $R^3$ is alkoxycarbonyl.

2. A compound of claim 1 wherein $R^3$ is alkyl, alkoxycarbonyl or

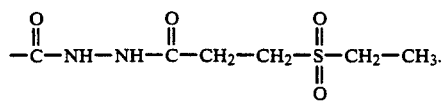

3. A compound of claim 2 wherein X is oxygen.
4. A compound of claim 3 wherein $R^1$ is hydrogen or halogen.
5. A compound of claim 4 wherein $R^2$ is hydrogen or halogen.
6. A compound of claim 5 wherein $R^1$ is halogen.
7. A compound of claim 6 wherein $R^2$ is hydrogen.
8. A compound of claim 1, wherein the compound is:

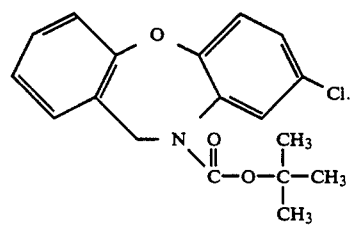

9. A compound of claim 1, wherein the compound is:

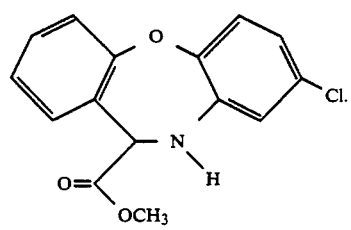

10. A compound of claim 1, wherein the compound is:

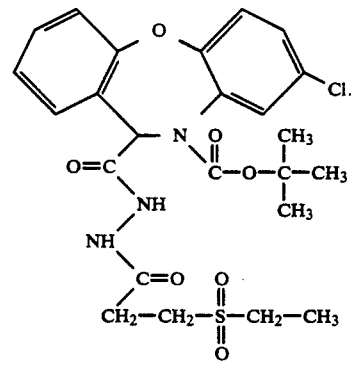

11. A pharmaceutical composition comprising a pharmaceutically-acceptable carrier and a therapeutically-effective amount of a compound of claim 1.

12. A method for treating pain in a mammal comprising administering to said mammal a therapeutically-effective amount of a compound of claim 1.

13. The pharmaceutical composition of claim 11 wherein the compound is:

8-chlorodibenz[b,f][1,4]oxazepine-10,11(11H)-dicarboxylic acid, 10-(1,1-dimethylethyl) ester, 11-[2-[3-(ethylsulfonyl)-1-oxopropyl]hydrazide].

14. The method of claim 12 wherein the compound is:
8-chlorodibenz[b,f][1,4]oxazepine-10,11(11H)-dicarboxylic acid, 10-(1,1-dimethylethyl) ester, 11-[2-[3-(ethylsulfonyl)-1-oxopropyl]hydrazide].

15. A compound having a structure:

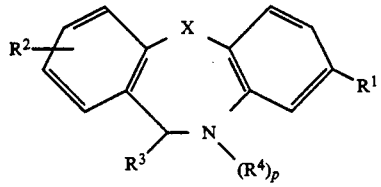

or a pharmaceutically-acceptable salt, ester or amide thereof, wherein:

X is oxygen, sulfur,

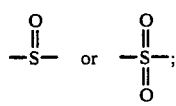

$R^1$ is hydrogen, halogen or haloalkyl;
$R^2$ is hydrogen, halogen, hydroxy or alkoxy;
$R^3$ is hydrogen, alkyl, carboxy, carboxamide,

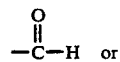

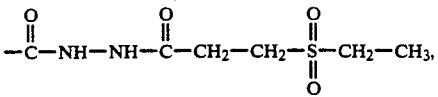

with the proviso that $R^3$ is not hydrogen or alkyl when $R^4$ is

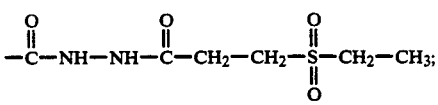

$R^4$ is alkoxycarbonyl or

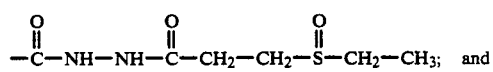

p is 0 or 1.

16. A pharmaceutical composition comprising a pharmaceutically-acceptable carrier and a therapeutically-effective amount of a compound of claim 15.

17. A method for treating pain in a mammal comprising administering to said mammal a therapeutically-effective amount of a compound of claim 15.

* * * * *

UNITED STATES PATENT AND TRADEMARK OFFICE
CERTIFICATE OF CORRECTION

PATENT NO. : 5,324,722  
DATED : June 28, 1994  
INVENTOR(S) : Hagen, et al.

Page 1 of 3

It is certified that error appears in the above-indentified patent and that said Letters Patent is hereby corrected as shown below:

Title page, line 12, reading "58,834" should read -- 058,834--.

Column 1, line 33, reading "fever,, such" should read -- fever, such --.

Column 2, line 5, reading "[b,f][1,4 oxazepine" should read -- [b,f][1,4]oxazepine --.

Column 2, line 5, reading "-carbonyl compounds" should read -- -carbonyl)hydrazine compounds. --.

Column 2, line 11, reading "[b,f][1,4 oxazepin" should read -- [b,f][1,4]oxazepin --.

Column 2, line 22, reading "[b,f][1,4 oxazepine" should read -- [b,f][1,4]oxazepine --.

Column 2, line 27, reading "[b,f][1,4 oxazepine" should read -- [b,f][1,4]oxazepine --.

Column 3, line 4, reading "840-844 (985)," should read -- 840-844 (1985) --.

Column 4, line 20, reading "Br. J Pharmac," should read -- Br. J. Pharmac., --.

Column 4, line 33, reading "George et al," should read -- George et al., --.

Column 5, line 24, reading "alkyl, carboxyl," should read -- alkyl, carboxy, --.

UNITED STATES PATENT AND TRADEMARK OFFICE
CERTIFICATE OF CORRECTION

PATENT NO. : 5,324,722
DATED : June 28, 1994
INVENTOR(S) : Hagen, et al.

It is certified that error appears in the above-indentified patent and that said Letters Patent is hereby corrected as shown below:

Column 5, line 26, reading "carboxamide," should read -- carboxamide, alkoxycarbonyl --.

Column 10, line 3, reading "J Pharm Sci.," should read -- J. Pharm. Sci., --.

Column 10, line 27, reading "Pharmaceutical Salts, supra.)" should read -- Pharmaceutical Salts," supra.) --.

Column 24, line 14, reading "hydogenated with" should read -- hydrogenated with --.

Column 24, line 34, reading "stirring compound" should read -- stirring solution --.

Column 24, line 42, reading "(MqSO$_4$)" should read -- (MgSO$_4$) --.

Column 30, line 53, reading "mouse orrat." should read -- mouse or rat. --.

Column 31, line 28, reading "Advances in Bio-chemicaI" should read -- Advances in Biochemicals --.

Column 33, line 38, reading "alkyl, carboxyl," should read -- alkyl, carboxy, --.

Column 33, line 40, reading "carboxamide," should read -- carboxamide, alkoxycarbonyl --.

UNITED STATES PATENT AND TRADEMARK OFFICE
CERTIFICATE OF CORRECTION

PATENT NO. : 5,324,722
DATED : June 28, 1994
INVENTOR(S) : Hagen, et al.

It is certified that error appears in the above-indentified patent and that said Letters Patent is hereby corrected as shown below:

Column 33, line 49, reading "wherein the proviso" should read -- with the proviso --.

Column 35, line 31, reading "carboxamide," should read -- carboxamide, alkoxycarbonyl, --.

Signed and Sealed this

Fifteenth Day of November, 1994

Attest:

BRUCE LEHMAN

Attesting Officer                    Commissioner of Patents and Trademarks